United States Patent [19]
Otten et al.

[11] Patent Number: 5,628,758
[45] Date of Patent: May 13, 1997

[54] MEDICAL INSTRUMENT FOR DIRECTED PLACEMENT OF A KNOT

[75] Inventors: Gert Otten, Schiffdorf; Carsten Lindeke, Berlin, both of Germany

[73] Assignee: Aerztliche Mechanik Udo Lindeke & Sohn, Berlin, Germany

[21] Appl. No.: 413,357

[22] Filed: Mar. 30, 1995

[30] Foreign Application Priority Data

Mar. 31, 1994 [DE] Germany .............. 44 11 827.9

[51] Int. Cl.⁶ ............................................. A61B 17/00
[52] U.S. Cl. .................. 606/148; 606/139; 606/207
[58] Field of Search .......................... 606/139, 144, 606/148, 205, 207; 289/17

[56] References Cited

U.S. PATENT DOCUMENTS

| | | |
|---|---|---|
| 2,433,956 | 1/1948 | Miller . |
| 2,595,086 | 4/1952 | Larzelere . |
| 3,834,395 | 9/1974 | Santos . |
| 3,840,003 | 10/1974 | Komiya ................................. 606/207 |
| 5,133,723 | 7/1992 | Li ............................................ 606/139 |
| 5,192,287 | 3/1993 | Fournier et al. . |
| 5,217,471 | 6/1993 | Burkhart . |
| 5,257,637 | 11/1993 | El Gazayerli ......................... 606/148 |
| 5,308,357 | 5/1994 | Lichtman ............................. 606/205 |
| 5,382,258 | 1/1995 | Chow ................................... 606/148 |
| 5,383,877 | 1/1995 | Clarke .................................. 606/148 |
| 5,439,470 | 8/1995 | Li .......................................... 606/148 |

FOREIGN PATENT DOCUMENTS

| | | |
|---|---|---|
| 649416 | 2/1979 | Russian Federation . |
| 733666 | 5/1980 | Russian Federation . |
| 820810 | 4/1981 | Russian Federation . |
| 2247841 | 3/1992 | United Kingdom . |
| WO94/08515 | 4/1994 | WIPO . |

*Primary Examiner*—Jeffrey A. Schmidt
*Attorney, Agent, or Firm*—McAulay Fisher Nissen Goldberg & Kiel, LLP

[57] ABSTRACT

A medical instrument for placement of a knot, in particular, for operating within closed spaces. With the use of such instrument, the thread can be held, guided and/or manipulated at least on one side of the knot and adjacent thereto by an instrument head in such a way that the knot can be pushed into the vicinity of a target point and placed exactly in the target point by spreading at least one free end of the thread.

20 Claims, 3 Drawing Sheets

MEDICAL INSTRUMENT FOR DIRECTED PLACEMENT OF A KNOT

BACKGROUND OF THE INVENTION a) Field of the Invention

The invention is directed to a medical instrument for the directed placement of a knot formed by two free ends of a surgical thread of like suture material accompanied by formation of a continuous loop.

b) Description of the Related Art

In medical practice, tissue, organs and the like are frequently joined by means of surgical thread by passing the thread through the tissue or looping it around the organ and then tightening the loop by means of a knot until the tissue or organ is held in the desired position. Often, an additional knot is then tied on the first knot in order to secure this position. Placing the knot is very difficult in particular when the suture line is poorly accessible. Placing the knot is especially problematic when operating within a closed space. For this purpose, after the loop is placed through the tissue or organ, the two free ends must be guided out of the body via a trocar and then knotted. An instrument is then used to move the knot through the trocar to the suture line while the free ends of the thread remain outside the trocar. Known instruments for sliding the knot have a long shaft having a holder or the like for the knot arranged at one end. The holder is guided to the knot between the two free ends of the thread until the knot is received therein or held in some other manner. The knot is then slid, first within the trocar and then within the body cavity, until reaching the suture line. Handling of the knot and the free ends of the thread is not always exact. Sometimes the knot or the ends of the thread cannot be held securely by the instrument and are lost so that the ends must be knotted again and the sliding of the knot must be repeated. A particular drawback consists in that the knot can, at best, be slid, but not placed and tightened in an exact manner.

OBJECT AND SUMMARY OF THE INVENTION

The primary object of the present invention is to provide a medical instrument of the type mentioned above which facilitates reliable handling of the knot and ends of the thread and enables an exact placement of the knot in poorly accessible suture lines.

According to the invention, this object is met in that the thread can be guided and handled so as to be held by an instrument head adjacent to the knot at least on one side of the knot so that the knot and the adjacent thread portions can be held securely, slid into the vicinity of a target point and then placed, i.e., tightened, in the target point in an exact manner by spreading out at least one free end of the thread. In this way, very precise, secure knots can be placed reliably and economically even in locations with extremely limited access.

In a special development, the instrument head is provided with at least one profile for separately holding, guiding or handling the free ends of the thread and/or the knot and the looped portions adjacent thereto so as to assist precise placement of the knot.

The profile of the instrument head advantageously has a peripheral region for the free ends of the thread. In addition, it is provided with a central region serving to receive the knot and the adjacent loop portions. The two regions are connected via a recess. The peripheral region permits the free ends of the thread to be manipulated separately and accordingly allows exact guidance of the knot on the instrument head. On the other hand, the recess makes it possible to move the knot sliding in the peripheral region into the central region in a continuous manner.

The recess penetrates the instrument head roughly vertically to its center line and preferably has an acute-angled cross section so that the knot and one of the free ends of the thread can be guided in a directed manner and separately by an open branch of the recess and separately by the other dead-end branch, respectively.

In a further development of the invention, the instrument head is divided into two halves which are movable relative to one another so that the free ends of the thread which are held by the respective halves are movable relative to one another.

It is provided in a special development that the halves are constructed in the manner of shears and are swivelable around an axis. The free ends can accordingly be spread apart from one another in such a way that the knot can creep toward the target point and be tightened and placed to a certain extent in this location.

Further features of the invention and their advantages are indicated in the patent claims and the description. The invention is explained more fully in the following with reference to an embodiment example.

DESCRIPTION OF THE PREFERRED EMBODIMENTS

Figure 1:
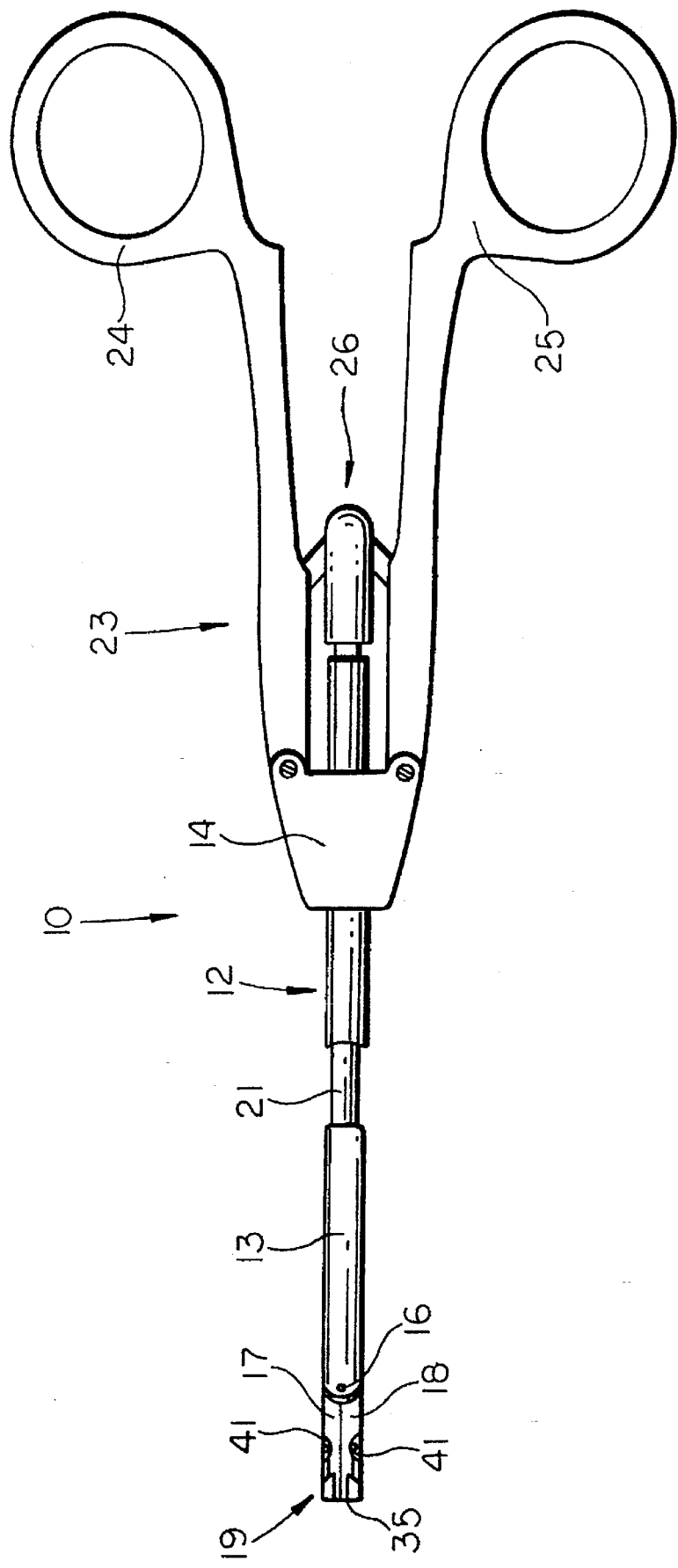
FIG. 1 illustrates a top view of an instrument for placing a knot.

A medical instrument 10 (FIG. 1) for directed placement of a knot 11 has a base body 12. One side of the base body 12 is formed by a guide sleeve 13 and the other side is formed by a support 14.

An axle pin 16 is arranged at an end region 15 of the guide sleeve 13, the two halves 17, 18 of a divided instrument head 19 being held so as to be swivelable relative to one another around this axle pin 16. The swiveling movement is effected by means of an actuating device 20 whose connecting rod 21 is held in the guide sleeve 13 so as to be displaceable axially. An end portion or side of the connecting rod 21, neither of which is shown in the drawing, is connected with each half 17, 18 of the instrument head 19 in each instance via a lever (not shown) somewhat in the manner of a folding lattice grate so that the swiveling movement of the halves 17, 18 is produced by the axial displacement of the connecting rod 21 within the guide sleeve 13.

A scissor-like grip member 23 with two grip halves 24, 25 which are swivelable relative to one another are associated with the support 14 of the base body 12 for handling the instrument 10 as a whole and for carrying out the axial displacement of the connecting rod 21 and accordingly the swiveling movement of the halves 17, 18 of the instrument head 19. A drive mechanism 26 constructed in the manner of a folding lattice grate is associated with the grip halves 24, 25 for the axial displacement of the connecting rod 21. This drive mechanism 26 is connected with the connecting rod 21 in such a way that a swiveling movement of the grip halves 24, 25 causes an axial displacement of the connecting rod 21.

The instrument head 19 has a substantially cylindrical shape. Its diameter corresponds approximately to that of the guide sleeve 13 and is dimensioned in such a way that the instrument head 19 and guide sleeve 13 are displaceable in a trocar so that there is sufficient room in an inner gap between the trocar and guide sleeve 13 for two free ends 27 of a surgical thread.

Figure 2:
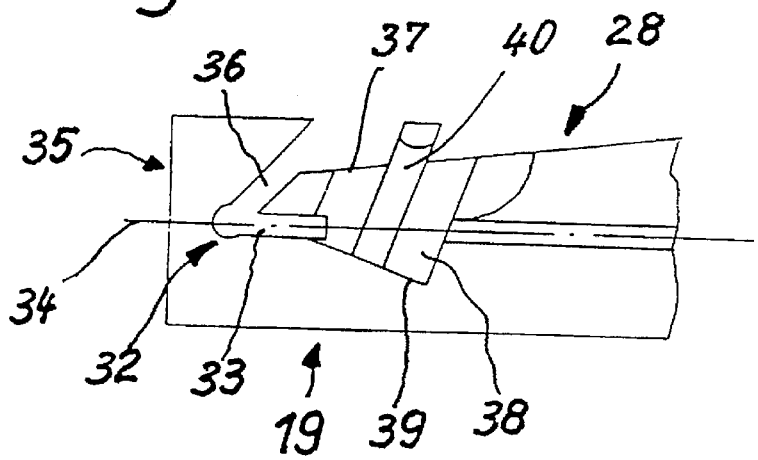
FIG. 2 illustrates an enlarged front view of an instrument head.
Figure 3:
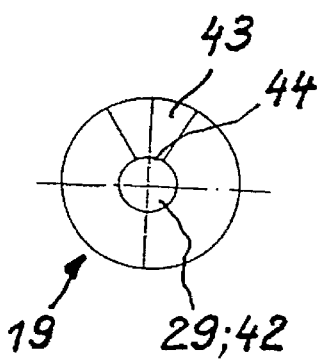
FIG. 3 illustrates a side view of the instrument head according to FIG. 2.

The instrument head 19 is provided with a profile (FIG. 2) having a peripheral region 28 for holding, guiding and handling the free ends 27 of the thread in particular and a central region 29 for holding a knot 31 made with the two free ends 27 so as to form a continuous loop 30. The peripheral and central regions 28, 29 are connected via a recess 32 penetrating the instrument head 19 roughly vertically to its center line 34. The recess has the shape and cross section of an acute angle. A dead-end branch 33 extends parallel to the center line 34 of the instrument head 19 approximately in the plane of the center line 34 until a front part 35 of the instrument head 19. The inner diameter or clear width of this branch 33 is so dimensioned that a free end 27 of the thread can be received and guided therein.

An open branch 36 of the recess 32 extends at an acute angle from an end region of branch 33 near the front part in the direction away from the front part 35 and exits from the instrument head 19. This branch 36 has a clear width allowing the knot 31 to pass through.

The peripheral region of the profile is provided with a bevel 37 which extends from the outer circumference of the instrument head 19 in the direction of the front part 35 at an inclination to the center line 34. The bevel 37 comprises roughly half of the instrument head 19 circumferentially and is curved in a uniform manner. It ends in the recess 32 on the side facing the front part approximately at the point where the branches 33, 36 merge.

A clearance grinding 38 with a cross section shaped like the segment of a circle is associated with the bevel 37 approximately symmetrically opposite the latter between its outlet at the circumference of the instrument head 19 and the location where it ends in the recess 32. This clearance grinding 38, which opens into the dead-end branch 33 of the recess 32 in the region of its base 39, extends from the base 39 to the center line 34 at a slight inclination facing away from the front part 35. A pin 40 extends from the base 39 parallel to the clearance grinding 38 so as to form a narrow slit 41 between the pin 40 and the clearance grinding 38, this slit 41 being open at the top. The length of the pin 40 is so dimensioned that it extends beyond the clearance grinding 38 and the bevel 37. However, the bevel 37 is dimensioned in such a way that the pins 40 do not project beyond the instrument head 19 in its radial direction so that the instrument head 19 can be displaced axially within a trocar without hindrance.

Figure 4:
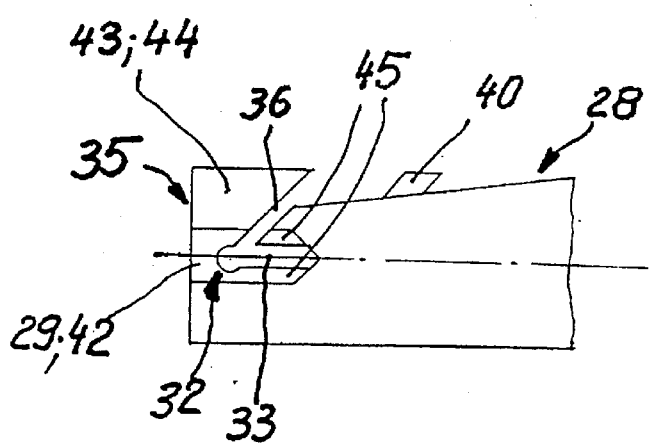
FIG. 4 illustrates an enlarged plan view of an inner surface of a half of the instrument head.
Figure 8:
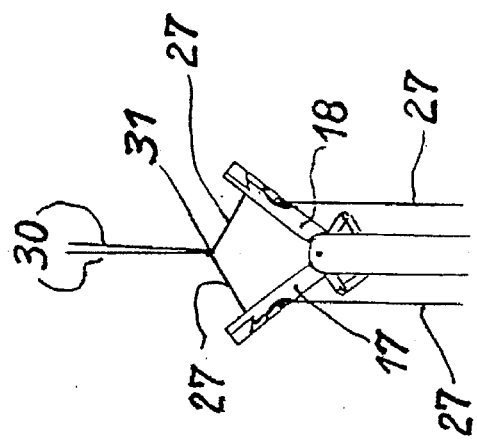
FIG. 8 illustrates a top view according to FIG. 1 showing the halves of the instrument head spread apart.
Figure 7:
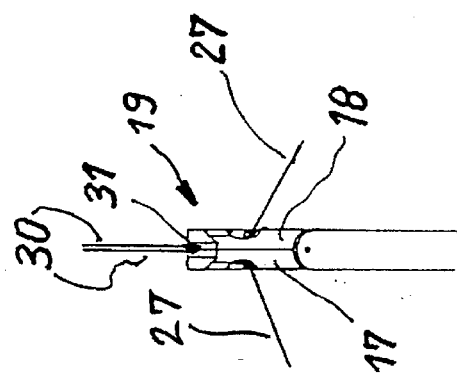
FIGS. 5 to 7 illustrate a top view according to FIG. 1 showing the knot in three different positions with respect to the instrument head.
Figure 6:
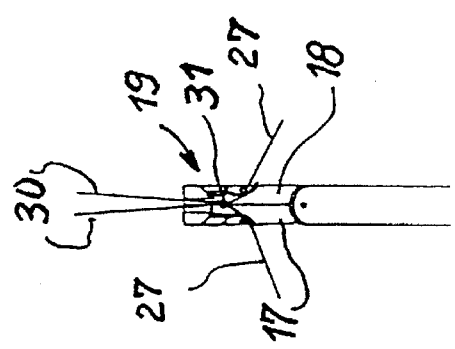

The central region 29 of the profile is formed by a bore hole 42 which is disposed coaxially to the instrument head 19, opens into the recess 32 and completely penetrates the branch 33 centrally (FIG. 4). The diameter of the bore hole 42 is greater than the clear width of branch 33 so that the bore hole 42 also has a lateral guide 45 in the region of branch 33 which securely holds the knot 31 in the bore hole 42. Further, the dimensions of the diameter of the bore hole 42 somewhat exceed those of the knot 31 in the radial direction of the instrument head 19.

Finally, a longitudinal slit 43 is associated with the bore hole 42, this longitudinal slit 43 extending in the front part 35 parallel to the center line 34 and symmetrically with respect to the bevel 37 and on the side of the latter. The longitudinal slit 43 is wedge-shaped and tapers from the circumference of the front part 35 to a narrow gap 44 by which it passes into the bore hole 42. In addition, the longitudinal slit 43 widens conically in the longitudinal direction of the instrument head 19 toward the end face of the front part 35, wherein the longitudinal slit 43 and gap 44 as well as the peripheral and central regions 28, 29 of the profile are associated in a symmetrical manner with the two halves 17, 18 of the instrument head 19.

The placement of the knot 31 by means of the instrument 10 is described in the following.

Figure 5:
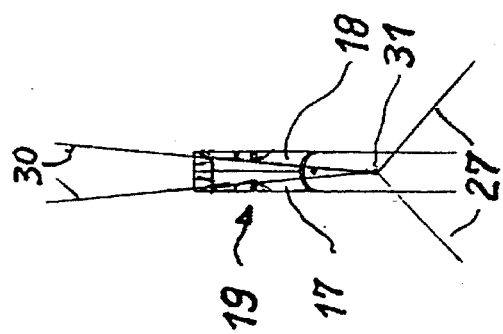

After the knot 31 has been tied by means of the free ends 27 of the thread while forming a loop 30 passing through the tissue or around an organ, the instrument 10 is positioned with respect to the knot 31 in such a way that the knot 31 is located on the guide sleeve 13 roughly in the center. The two free ends 27 are held laterally approximately around the guide sleeve 13 so as to be spread apart from one another (FIG. 5). The free ends are held under slight tension so that the thread is tightened as a whole. The instrument 10 is then guided in such a way that the knot 31 arrives at the instrument head 19 and slides down its bevel 37 in the direction of the front part 35. In this way, the free ends 27 are engaged by the pins 40 and guided into the slit 41, while the regions of the loop 30 which are adjacent to the knot 31 pass into the longitudinal slit 43, which is assisted by the conical shape of the longitudinal slit 43 described above. For reliable placement of the free ends 27 in the slit 41, it is advisable to wrap the two free ends 27 somewhat further around the instrument head 19. Thus, the movement of the instrument 10 is effected away from the actual suture line until the knot 31 has slid down the bevel 37 until it enters the branch 36 of the recess 32, passes through the latter and finally arrives in the bore hole 42 of the central region 29 of the profile. In so doing, it is constantly held by the two free ends 27 in the center with respect to the bevel 37. At approximately the same time, the free ends 27, guided by the respective pin 40, reach the base 39 of the clearance grinding 38 and enter the recess 32 laterally. Meanwhile, the adjacent loop regions slide along the longitudinal slit 43 and the gap 44 into the bore hole 42.

When this position is reached, the movement of the instrument 10 is reversed in that it is now moved in the direction of the actual suture line. In so doing, the knot 31 in the bore hole 42 initially slides along the branch 33 and is held by the lateral guide 45 until it reaches the end of the bore hole 42. Next, the knot 31 which is reliably fixed in this way, is displaced. This displacement continues until the knot 31 arrives in the immediate vicinity of the target point, wherein this displacement can be effected very easily due to the guidance of the free ends 27 and the tightened thread. The actual placement of the knot 31 is then effected precisely in the target point in that the two halves 17, 18 of the instrument head 19 are swiveled relative to one another around the axle pin 16 by means of the actuating device 20 in such a way that the free ends 27 held by them are spread apart. The final movement of the knot 31 toward the target point and the tightening of the knot 31 are completed by means of this spreading. The tightening can be further assisted by increasing somewhat the tension on the free ends after the halves 17, 18 have been spread apart. It is essential that the free ends 27 and the knot 31 are held securely and separately in each phase by the instrument head 19.

After the knot 31 has been placed, the halves 17, 18 are brought together again by means of the actuating device 20, whereupon the instrument 10 can be freely withdrawn or pulled out of the trocar. The free ends 27 slide within the respective gap 44, recess 32 and bore hole 39 until exiting from the instrument head. Finally, the respective free end 27 can be cut at a suitable location.

While the foregoing description and drawings represent the preferred embodiments of the present invention, it will be obvious to those skilled in the art that various changes and modifications may be made therein without departing from the true spirit and scope of the present invention.

What is claimed is:

1. A medical instrument for directed placement of a knot formed by two free ends of a surgical thread or the like suture material accompanied by formation of a continuous loop, comprising:

an instrument head for holding, guiding and/or manipulating the surgical thread at least on one side of the knot and adjacent thereto in such a way that the knot can be pushed into the vicinity of a target point and placed exactly in the target point by spreading at least one free end of the thread, said instrument head having a profile for separately holding, guiding and/or handling at least one of the free ends of the thread and the knot and the adjacent portions of the loop and wherein the profile has at least one peripheral region for the free ends and a central region for the knot and their adjacent loop portions and wherein the peripheral and central regions are connected via a recess, said peripheral region having a bevel, for supporting the knot and the free ends, which extends from the outer circumference of the instrument head in the direction of a front part of the instrument head and toward the center line of the instrument head, said bevel ending in the recess.

2. The medical instrument according to claim 1, wherein the recess penetrates the instrument head roughly at a right angle to a center line thereof and is constructed in cross section in the shape of an acute angle.

3. The medical instrument according to claim 1, wherein a dead-end branch of the recess for receiving the free ends extends in the longitudinal direction of the instrument head roughly along the center line of the latter as far as a front part of the instrument head.

4. The medical instrument according to claim 3, wherein another branch of the recess for receiving and guiding at least the knot extends from the end of said dead-end branch on the front part side away from the front part at an acute angle and exits from the instrument head.

5. The medical instrument according to claim 4, wherein the branches are dimensioned in such a way that the free ends of the thread can pass through the dead-end branch and the knot can pass through the other branch.

6. The medical instrument according to claim 1, wherein the central region has a bore hole coaxial to said instrument head for receiving at least the knot in a front part of the instrument head, which bore hole opens into the recess.

7. The medical instrument according to claim 6, wherein the diameter of the bore hole is slightly greater than the extent of the knot in the radial direction of the instrument head.

8. The medical instrument according to claim 6, wherein a wedge-shaped longitudinal slit is associated with the bore hole in the front part of the instrument head, said longitudinal slit tapering toward the bore hole until the formation of a narrow gap allowing the portions of the loop adjacent to the knot to pass into the bore hole.

9. The medical instrument according to claim 8, wherein the longitudinal slit also widens conically in the longitudinal direction of the instrument head toward the end face of the front part.

10. The medical instrument according to claim 8, wherein the instrument head has a peripheral region and a central region, the peripheral region having a bevel for supporting the knot and wherein the longitudinal slit and the bevel are associated corresponding to the circumference of the instrument head and are substantially disposed one after the other symmetrically in the longitudinal direction.

11. The medical instrument according to claim 1, wherein the instrument head is divided and has two halves which are movable relative to one another and wherein the halves are swivelable relative to one another and the profile and a longitudinal slit are associated with the halves in a symmetrical manner.

12. The medical instrument according to claim 11, wherein the halves are arranged in the manner of scissors and are swivelable about an axle pin associated with an end region of a guide sleeve of a base body such that the free ends of the thread can be spread apart.

13. The medical instrument according to claim 11, including an actuating device for moving the halves.

14. The medical instrument for directed placement of a knot formed by two free ends of a surgical thread or the like suture material accompanied by formation of a continuous loop, comprising:

an instrument head for holding, guiding and/or manipulating the surgical thread at least on one side of the knot and adjacent thereto in such a way that the knot can be pushed into the vicinity of a target point and placed exactly in the target point by spreading at least one free end of the thread, said instrument head having a profile for separately holding, guiding and/or handling at least one of the free ends of the thread and the knot and the adjacent portions of the loop wherein the instrument head has a profile with a peripheral region and central region, which regions end in a recess having branches said peripheral region having a bevel, for supporting the knot and the free ends, which extends from the outer circumference of the instrument head in the direction of the front part and toward the center line of the instrument head and ends in the recess approximately at the point where the branches merge;

wherein one branch of the recess for receiving the free ends is a dead-end branch which extends in the longitudinal direction of the instrument head roughly along the center line of the latter as far as a front part of the instrument head and wherein another branch of the recess for receiving and guiding at least the knot extends from the end of said dead-end branch on the front part side away from the front part at an acute angle and exits from the instrument head.

15. The medical instrument according to claim 14, wherein the bevel is curved along the circumference roughly along half of the instrument head in an approximately uniform manner.

16. The medical instrument according to claim 15 including a base, wherein both sides of the bevel are provided with a clearance grinding which opens into the dead-end branch of the recess in the region of said base.

17. The medical instrument according to claim 16, wherein the clearance grinding extends at a slight inclination from the base to the center line of the instrument head in the direction away from the front part.

18. The medical instrument according to claim 16, wherein a pin, which is arranged substantially parallel to the clearance grinding, extends from the base of the clearance grinding and a slit which is open on one side is formed between the clearance grinding and the pin, and a free end of the thread can be inserted into and guided in the slit.

19. The medical instrument according to claim 18, wherein the pin has a length which is so dimensioned that it projects beyond the clearance grinding and the bevel, but does not project beyond the instrument head in the radial direction of the latter.

20. The medical instrument for directed placement of a knot formed by two free ends of a surgical thread or the like suture material accompanied by formation of a continuous loop, comprising:

an instrument head for holding, guiding and/or manipulating the surgical thread at least on one side of the knot and adjacent thereto in such a way that the knot can be pushed into the vicinity of a target point and placed exactly in the target point by spreading at least one free end of the thread, said instrument head having a profile for separately holding, guiding and/or handling at least one of the free ends of the thread and the knot and the adjacent portions of the loop and wherein the profile has at least one peripheral region for the free ends and a central region for the knot and their adjacent loop portions and wherein the peripheral and central regions are connected via a recess;

wherein a dead-end branch of the recess for receiving the free ends extends in the longitudinal direction of the instrument head roughly along the center line of the latter as far as a front part of the instrument head and wherein another branch of the recess for receiving and guiding at least the knot extends from the end of said dead-end branch on the front part side away from the front part at an acute angle and exits from the instrument head, and wherein the central region has a bore hole coaxial to said instrument head for receiving at least the knot in a front part of the instrument head, which bore hole opens into the recess and wherein the diameter of the bore hole is greater than the clear width of the dead-end branch and the bore hole completely penetrates the branch in the axial direction of the instrument head in such a way that a lateral guide for the knot is formed along the bore hole.

* * * * *